United States Patent [19]

Tsukamoto et al.

[11] Patent Number: 4,799,789
[45] Date of Patent: Jan. 24, 1989

[54] CHROMATIC DISPERSION MEASURING SYSTEM FOR OPTICAL FIBERS

[75] Inventors: Takeshi Tsukamoto, Hadano; Takao Tanimoto, Sagamihara; Hidetoshi Miyao, Yokohama, all of Japan

[73] Assignee: Anritsu Corporation, Tokyo, Japan

[21] Appl. No.: 159,888

[22] Filed: Feb. 24, 1988

[30] Foreign Application Priority Data

Feb. 27, 1987 [JP] Japan ............................ 62-27436[U]
Mar. 9, 1987 [JP] Japan .................... 62-52130

[51] Int. Cl.$^4$ ........................................... G01N 21/84
[52] U.S. Cl. .................................................. 356/73.1
[58] Field of Search ........................................ 356/73.1

[56] References Cited

U.S. PATENT DOCUMENTS 4,551,019 11/1985 Vella et al. ..................... 356/73.1

OTHER PUBLICATIONS

The Paper 2188 of 1984 All National Meeting of Electronics and Communications Engineers of Japan, entitled "Chromatic Dispersion Measurement for Singlemode Fiber", Tanaka & Kitayama.

*Primary Examiner*—Vincent P. McGraw
*Attorney, Agent, or Firm*—Frishauf, Holtz, Goodman & Woodward

[57] ABSTRACT

A system for measuring a chromatic dispersion of an optical fiber based on a baseband phase comparison method has an optical signal transmitter, a reference optical fiber, a measurement optical fiber, and an optical signal receiver. The transmitter has n light sources for selectively generating, as measurement optical signals, optical signals having wavelengths corresponding to n wavelength points to be measured. One of the n light sources also serves to generate a reference optical signal. The transmitter further has an optical switch. The optical switch has n optical signal inputs arranged in correspondence with the n light sources, a measurement optical signal output, and a reference optical signal output. The optical switch commonly outputs, to the measurement optical signal output, the measurement optical signal which is output from the designated one of the n light sources and is selectively input to the n optical signal inputs. A half mirror is provided for outputting the reference optical signal generated by one of the n light sources to the reference signal output. The optical signal receiver is coupled to the reference optical fiber and the measurement optical fiber, and receives the reference optical signal from the reference optical fiber and the measurement optical signal from the measurement optical fiber, respectively, for measuring chromatic dispersion. The receiver includes a plurality of programmable optical attenuators.

25 Claims, 6 Drawing Sheets

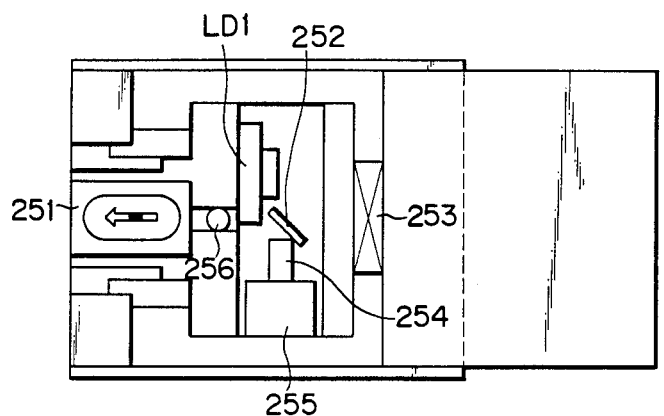
F I G. 4A
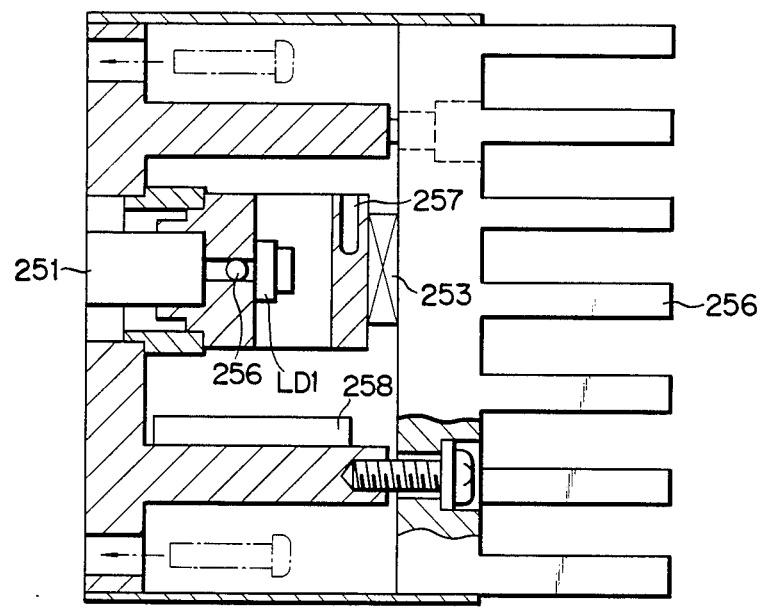
F I G. 4B

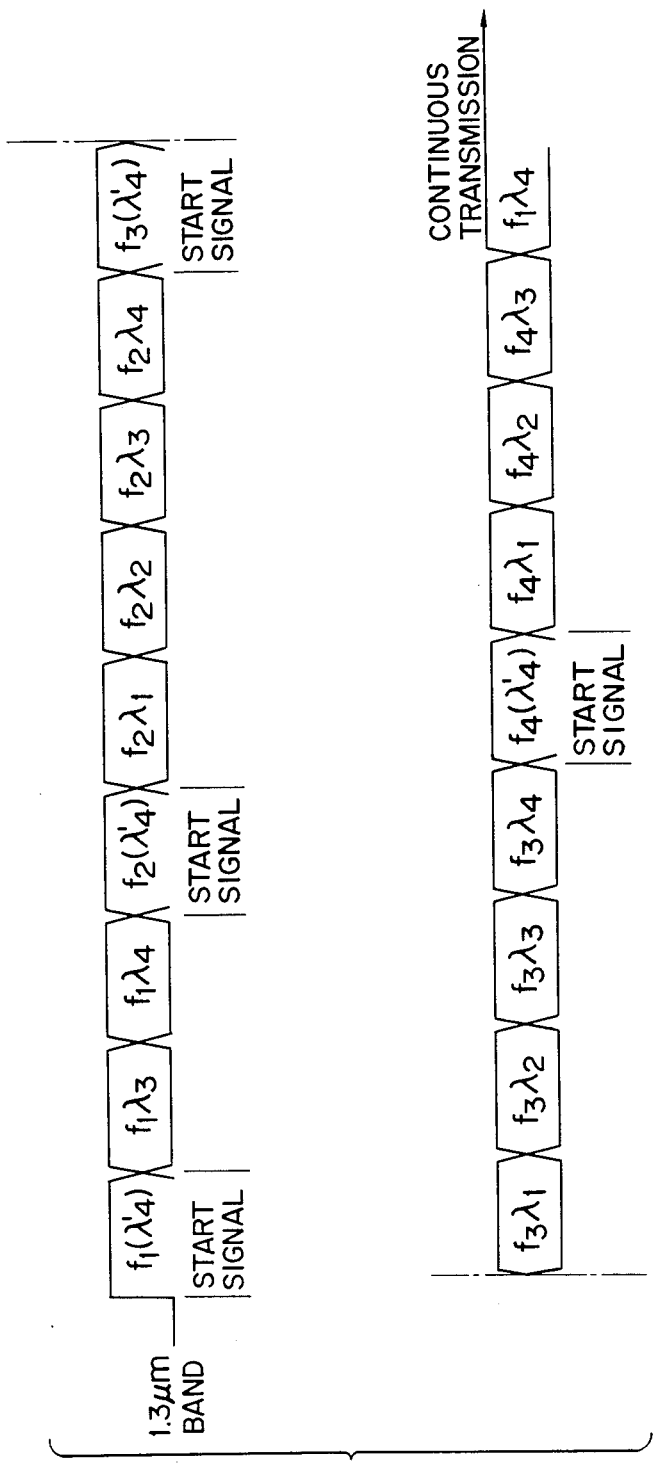
F I G. 6A

CHROMATIC DISPERSION MEASURING SYSTEM FOR OPTICAL FIBERS

BACKGROUND OF THE INVENTION

1. Field of the Invention

The present invention relates to a system for measuring chromatic dispersion of an optical fiber and, more particularly, to a system for measuring chromatic dispersion of an optical fiber by a baseband phase comparison method.

2. Description of the Related Art

The chromatic dispersion characteristics of optical fibers are important for determining an information transmission speed of an optical fiber communication path. The following are the main methods used at present for measuring chromatic dispersion in single-mode optical fibers:

(1) A pulse delay time difference measurement method using a fiber Raman laser/spectroscope combination;

(2) A baseband phase comparison method using an LED (light-emtting diode)/spectroscope combination;

(3) A baseband phase comparison method using multiple LDs (laser diodes) of different wavelengths; and (4) An interference method using the interference characteristics of light.

Of these methods, the baseband phase comparison method (3) will be described below. In general, optical signals having different wavelengths differ in group velocity due to material dispersion and waveguide dispersion, resulting in phase differences of the optical signals after their propagation through an optical fiber. The baseband phase comparison method utilizes this fact. Optical signal generators such as LDs having different wavelengths are arranged in an optical signal transmitter, and two types of optical signals, i.e., a reference optical signal and a measurement optical signal, which are intensity-modulated by a sine wave modulation signal, are generated. The two types of optical signals are incident on a reference optical fiber and a measurement optical fiber, respectively. In an optical signal receiver, a group delay time difference is calculated from a phase difference between the wavelengths after propagation through the measurement optical fiber. The measurement result is approximated by appropriate function $\tau(\lambda)$, and the function is analytically differentiated to obtain target chromatic dispersion characteristics $D(\lambda) = d\tau(\lambda)/d\lambda$. The graph in FIG. 2 represents the relationship between the group delay time difference and the wavelengths.

However, in the conventional chromatic dispersion measuring system using the baseband phase comparison method described above, a special-purpose light source, e.g., an LD is separately arranged in order to obtain the reference optical signal in addition to the measurement optical signal generators. This fact is disadvantageous in realizing a compact measurement apparatus. In addition, since a very expensive LD and associated elements must be additionally used, this interferes with reduction in cost.

Furthermore, the optical signal receiver of the conventional chromatic dispersion measuring system has a photoelectric conversion section for converting optical signals emerged from the measurement fiber and the reference fiber into electrical signals. Thus, the conventional system has a function of converting an optical signal within a predetermined level range into an electrical signal with good linearity but cannot covert the optical signal exceeding the predetermined level range into an electrical signal with good linearity. For this reason, when the optical signal level is expected to change greatly, a maunal optical attenuator or the like is provided to the input side of the photoelectric conversion section to keep the optical signal level within a predetermined range.

Such a manual attenuation value adjusting method is not satisfactory in terms of a measurement time. A loss caused by a difference between the lengths of fibers to be measured or by a coupling state varies. Therefore, when an unexpected change in optical signal level occurs, it is difficult to appropriately adjust the optical signal level. And this leads to degradation of light receiving elements.

SUMMARY OF THE INVENTION

It is therefore an object of the present invention to provide a low-cost, compact chromatic dispersion measuring system in which the number of optical signal generators necessary for an optical signal transmitter is reduced.

It is another object of the present invention to provide a chromatic dispersion characteristic measuring system which can automatically adjust the level of an optical signal emerged from an optical fiber, and can convert the optical signal into an electrical signal with good linearity in addition to the above-mentioned advantages.

According to the present invention, there is provided a system for measuring a chromatic dispersion of an optical fiber based on a baseband comparison method. The system comprises a light signal transmitter, a light signal receiver, a reference optical fiber, and a measurement optical fiber. The transmitter comprises n light source means for selectively generating optical signals having wavelengths corresponding to n wavelength points to be measured. One of the n light source means also serves to generate a reference optical signal. The transmitter also comprises modulation signal generating means for generating at least one modulation signal having a predetermined frequency, and first control signal generating means for designating the n light source means in a predetermined order in order to generate the measurement optical signals and the reference optical signal. The transmitter further comprises light source switching means. The light source switching means is connected between the first control signal generating means, the modulation signal generating means, and the n light source means, and selectively supplies the modulation signal to a specific one of the n light source means which is designated by the first control signal to generate the measurement optical signal and to the light source which also serves to generate the reference optical signal, or only to the light source which serves to generate both the measurement optical signal and the reference optical signal. The transmitter further comprises second control signal generating means for generating a second control signal having a predetermined synchronous relationship with the first control signal. The transmitter also comprises optical switch means. The optical switch means has n optical signal inputs corresponding to the n light source means, a measurement optical signal output, and a reference optical signal output. In response to the second control signal from the second control signal generating means, the optical switch means commonly outputs, to the measurement optical signal output, the measurement optical signal which is output from the designated one of the n light source means and is selectively input to the n optical signal inputs, and outputs the reference signal generated by one of the n light source means to the reference optical signal output. The receiver means, which is connected to the reference optical fiber and the measurement optical fiber, receives the reference optical signal emerged from the reference optical fiber and the measurement optical signal emerged from the measurement optical fiber to measure chromatic dispersion. The receiver means includes a plurality of programmable optical attenuator means.

BRIEF DESCRIPTION OF THE DRAWINGS

Various advantages of the present invention will become apparent to one skilled in the art upon reading the following specification and by reference to the following drawings in which:

FIGS. 4A and 4B are views showing an arrangement of a light source used in the chromatic dispersion measuring system of the present invention;

FIGS. 6A and 6B are timing charts showing transmission timings of a modulation signal, and respectively showing a case wherein a 1.3-$\mu$m band zero dispersion wavelength optical fiber is used and a case wherein a 1.55-$\mu$m band zero dispersion wavelength optical fiber is used.

DETAILED DESCRIPTION OF THE PREFERRED EMBODIMENTS

Figure 1:
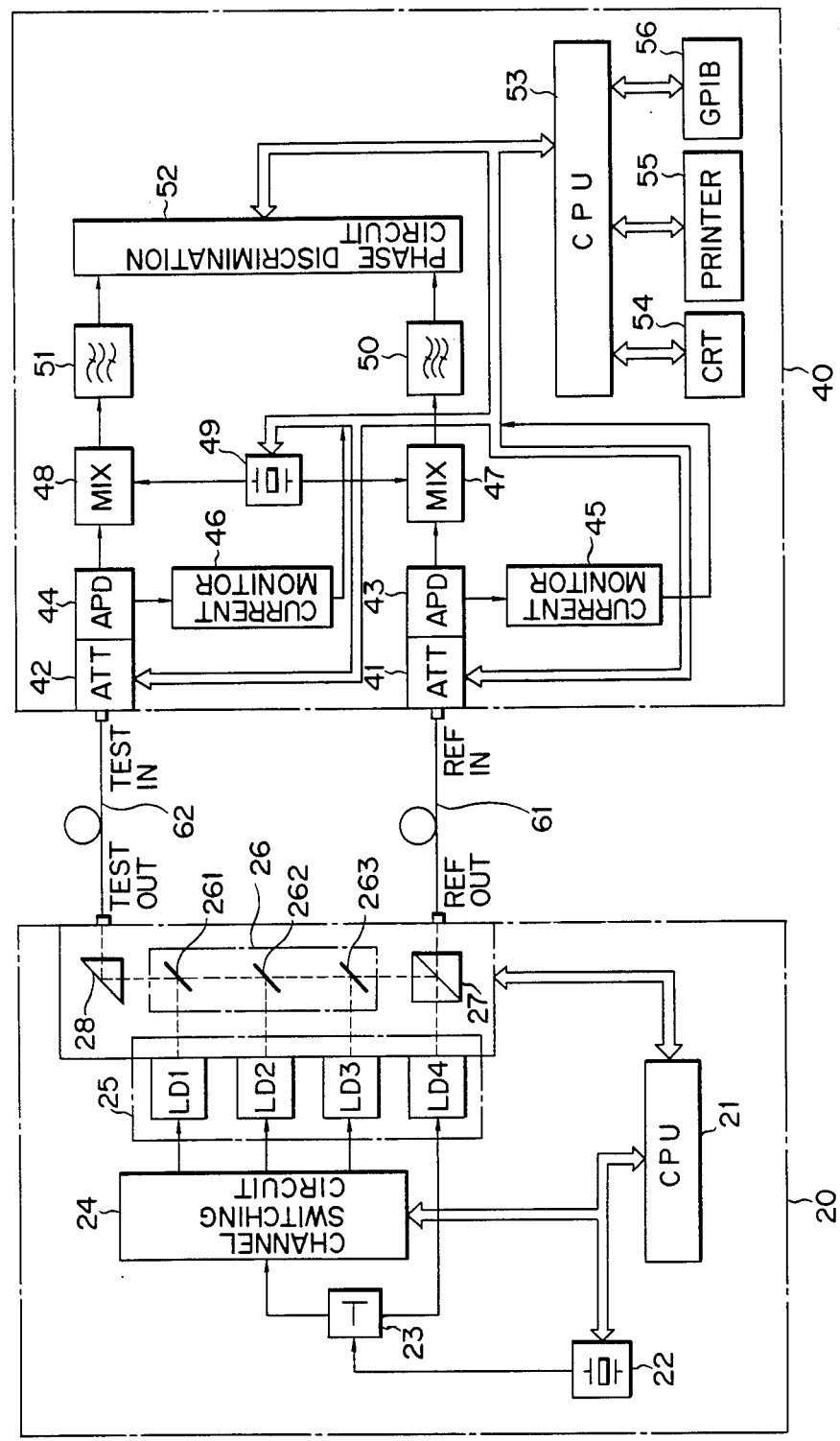
FIG. 1 is a block diagram showing a chromatic dispersion measuring system according to an embodiment of the present invention.

Referring to FIG. 1, one end of reference optical fiber 61 is connected to reference optical signal output terminal REF OUT of optical signal transmitter 20 of a chromatic dispersion measuring system of the present invention. One end of measurement optical fiber 62 is connected to measurement optical signal output terminal TEST OUT of transmitter 20. The other end of reference fiber 61 is connected to reference optical signal input terminal REF IN of optical signal receiver 40 of the system of the present invention, and the other end of measurement fiber 62 is connected to measurement optical signal input terminal TEST IN of receiver 40.

Transmission section 20 of the chromatic dispersion measuring system of the present invention will be described by referring to FIG. 1. Modulation signal generating circuit 22 comprises four quartz oscillators having four different oscillation frequencies f1 to f4. Circuit 22 is connected to 2-branching circuit 23 comprising a resistor. One output terminal of circuit 23 is connected to channel switching circuit 24 with three outputs comprising a high-frequency relay matrix, and the other output terminal thereof is connected to laser diode LD4 of light source group 25 consisting of four laser diodes LD1 to LD4. Drive selection of the four quartz oscillators is performed in response to a selection signal from CPU 21. A switching operation by channel switching circuit 24 is also controlled by a switching instruction from CPU 21. In this system, 5, 50, 200, and 800 MHz are used as four frequencies f1 to f4. However, the present invention is not limited to these frequencies, and other frequencies may be employed. As described above, 2-branching circuit 23 comprises the resistor, and channel switching circuit 24 comprises the high-frequency relay matrix. However, these circuits may comprise other proper elements. Laser diodes LD1 to LD3 of light source group 25 are arranged at the output side of channel switching circuit 24. Optical switch group 26, i.e., 261 to 263 are arranged to face the output terminals of laser diodes LD1 to LD3, respectively. Half mirror 27 is arranged at the output side of laser diode LD4 in association with optical switches 261 to 263. Furthermore, prism 28 is arranged in association with optical switches 261 to 263. Light source group 25 comprises laser diodes LD1 to LD4 but may comprise other proper light sources.

The number of laser diodes used in the chromatic dispersion measuring system of the present invention is not limited to four. The wavelengths of laser diodes LD1 to LD4 are respectively 1.26, 1.30, 1.34, and 1.53 $\mu$m in a 1.3-$\mu$m band zero dispersion wavelength optical fiber, and are respectively 1.50, 1.53, 1.56, and 1.59 $\mu$m in a 1.55-$\mu$m band zero dispersion wavelength optical fiber. However, other proper wavelengths may be employed.

FIGS. 4A and 4B show a detailed arrangement of light source group 25. Each of light source group 25 includes optical isolator 251 for removing noise generated by the influence of light reflected by a corresponding one of laser diodes LD1 to LD4, spherical lens 256, mirror 252, Peltier element 253, light receiving element 255, SELFOC lens 254, thermistor 257, heat dissipating fin 256, and modulation circuit 258, in addition to laser diode, e.g., LD1. These elements including laser diodes LD1 to LD4 are very expensive, and hence, a reduction in the number of light source sections greatly influences the total cost performance.

Figure 5:
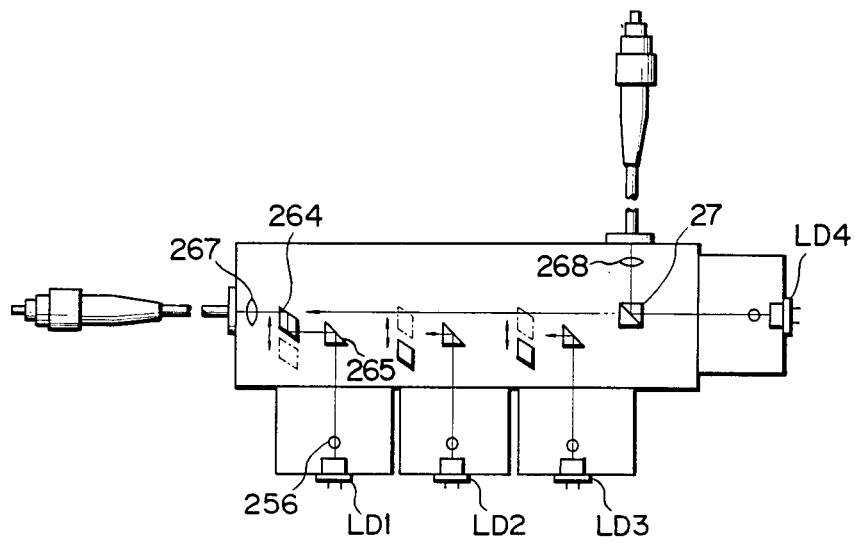
FIG. 5 is a view showing an arrangement of an optical switch used in the chromatic dispersion measuring system of the present invention.

As shown in FIG. 5, each of optical switches 261 to 263 comprises parallelogram prism, e.g., 264 arranged to shield an optical path between half mirror 27 and measurement fiber, and triangular prism, e.g., 265 arranged to be slightly shifted from parallelogram prism 264. These two prisms are arranged at positions such that light emitted from laser diodes LD1 to LD3 becomes incident on one end of measurement fiber through triangular prism 265 and parallelogram prism 264. When the light emitted from the laser diodes is reflected by half mirror 27 and is directed toward measurement fiber, parallelogram prism 264 is slid and shifted to release the optical path which has been shielded. Thus, the light can propagate straight from half mirror 27 to measurement fiber. Reference numeral 256 in FIG. 5 denotes a spherical lens. Reference numerals 267 and 268 denote a condensing lens.

Figure 3:
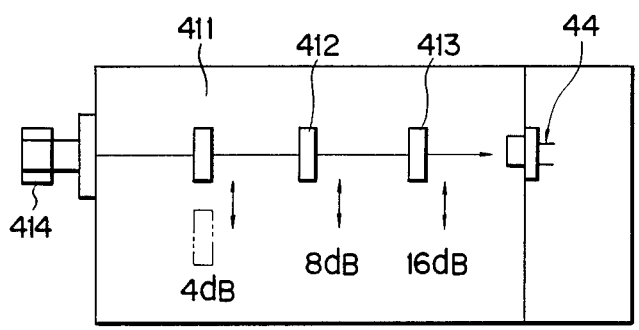
FIG. 3 is a view showing an arrangement of an attenuator according to the present invention.

In optical signal receiver 40 shown in FIG. 1, programmable ATTs (programmable attenuators) 41 and 42, are arranged at reference signal input terminal REF IN and measurement signal input terminal TEST IN of fibers 61 and 62, respectively. FIG. 3 shows more detailed attenuators 41 and 42. In each of programmable optical attenuator 41 and 42, three optical attenuation elements 411, 412, and 413 are serially arranged and are integrally coupled to, e.g., APD 44. Reference numeral 414 in FIG. 3 denotes a photoreceptacle. The diameter of each of optical attenuation elements 411, 412, and 413 is 8 mm, and attenuation values of these elements are respectively 4 dB, 8 dB, and 16 dB. However, the diameter and the attenuation values may be appropriately determined. These attenuation elements 411, 412, and 413 are programmably turned on/off, so that 8 different attenuation values can be set.

In FIG. 1, APDs 43 and 44 have a function of converting optical signals output from rogrammable optical attenuators 41 and 42 into electrical signals. Current monitors 45 and 46 are connected to APDs 43 and 44, respectively. Current monitors 45 and 46 recieve the electrical signals from APDs 43 and 44 to detect their signal levels, and control attenuation values of attenuators 41 and 42 in accordance with the detected levels, so that optical signals of a predetermined level can always be input to APDs 43 and 44. Demodulation signals converted photoelectrically at APDs 43 and 44 are input to mixers 47 and 48. Local signal generating circuit 49 comprises four quartz oscillators having four different oscillation frequencies f1' to f4'. Drive selection of the four quartz oscillators is performed in response to a selection signal from CPU 53. Mixers 47 and 48 perform frequency conversion using a local signal of a selected frequency. The converted electrical signal is supplied to phase discrimination circuit 52 in order to measure a phase difference between wavelengths.

For the sake of best understanding of the operation of the chromatic dispersion measuring system of the present invention, the operation procedures of overall system will be described with reference to FIG. 1. CPU 21 supplies a signal selection instruction to modulation signal generating circuit 22 based on a predetermined timing, and causes it to generate, e.g., modulation signal f1 (f1=5 MHz). Modulation signal f1 is branched into two by 2-branching circuit 23, and one output from circuit 23 is supplied to relay matrix circuit 24. Relay matrix circuit 24 performs the switching operation to select one of the outputs of channel switching circuit 24 in response to a switching instruction from CPU 21. Upon receiving the selected output, one of laser diodes LD1 to LD3 corresponding to the selected output, e.g., laser diode LD1 is driven. Thus, laser diode LD1 generates an optical signal which is intensity-modulated by modulation frequency f1. The optical signal is received by optical switch 261 corresponding to laser diode LD1. As described above, optical switch 261 is selected in response to the switching instruction from CPU 21. Thereafter, the optical signal is reflected by prism 28, and is incident on one end of measurement fiber 62 through measurement optical signal output terminal TEST OUT of optical signal transmitter 20, as a measurement optical signal. On the other hand, the other output of 2-branching circuit 23 is directly input to laser diode LD4. Therefore, laser diode LD4 outputs an optical signal which is intensity-modulated by modulation frequency f1. The generated optical signal is branched into two by half mirror 27. One signal is incident on one end of reference fiber 61 through reference optical signal output terminal REF OUT, while the other signal goes to prism 28 through optical switches 261 to 263 to reflect it toward one end of measurement fiber 62 through measurement optical signal output terminal TEST OUT of transmitter 20.

CPU 21 supplies the channel switching instruction to channel switching circuit 24 and optical switches 261 to 263 to select a new output of channel switching circuit 24. Therefore, one of laser diodes LD2 and LD3 excluding LD1, e.g., LD2, is driven upon input of modulation signal f1. The optical signal generated by LD2 is reflected by the corresponding optical switch, e.g., 262, and propagates toward prism 28. The optical signal reflected by prism 28 is incident on one end of measurement fiber 62 through measurement optical signal output terminal TEST OUT.

CPU 21 supplies the switching instruction to channel switching circuit 24 and optical switches 26 until all laser diodes LD1 to LD4 are selected. Thus, the reference optical signal and measurement optical signal are repetitively input to fibers 61 and 62 until all laser diodes LD1 to LD4 are selected.

After this repetitive operation is completed, CPU 21 supplies a new selection instruction to modulation signal generating circuit 22. In response to the instruction, the quartz oscillator having a frequency different from modulation frequency f1, e.g., f2=50 MHz, is driven, and the above repetitive operation is executed for frequency f2. Similarly, the repetitive operation is executed for frequency f3=200 MHz and for frequency f4=800 MHz.

Figure 6B:
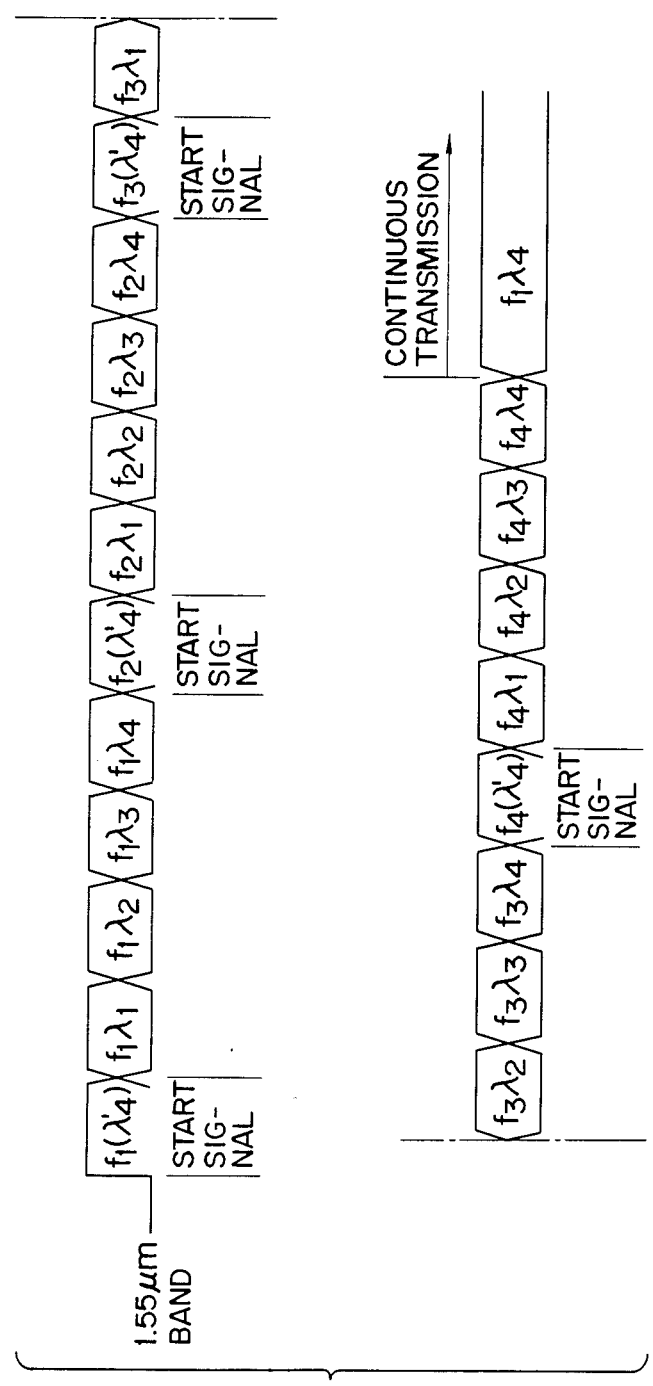

FIGS. 6A and 6B are timing charts showing states wherein modulation signals f1 to f4 are sequentially transmitted in association with the above repetitive operation. FIG. 6A exemplifies a 1.3-$\mu$m band zero dispersion wavelength optical fiber, and FIG. 6B exemplifies a 1.55-$\mu$m band zero dispersion wavelength optical fiber.

The receiver will be described. The reference optical signal and measurement optical signal respectively output from reference optical fiber 61 and measurement optical fiber 62 are received by APDs 43 and 44 while signal levels are controlled by programmable optical attenuators 41 and 42. The output signals from APDs 43 and 44 are input to mixers 47 and 48, respectively. Mixers 47 and 48 frequency-convert the input signals using a local signal having one of frequencies f1'-f4' generated by local signal generating circuit 49. After the conversion, the signals are supplied to phase discrimination circuit 52 through filters 50 and 51.

Figure 2:
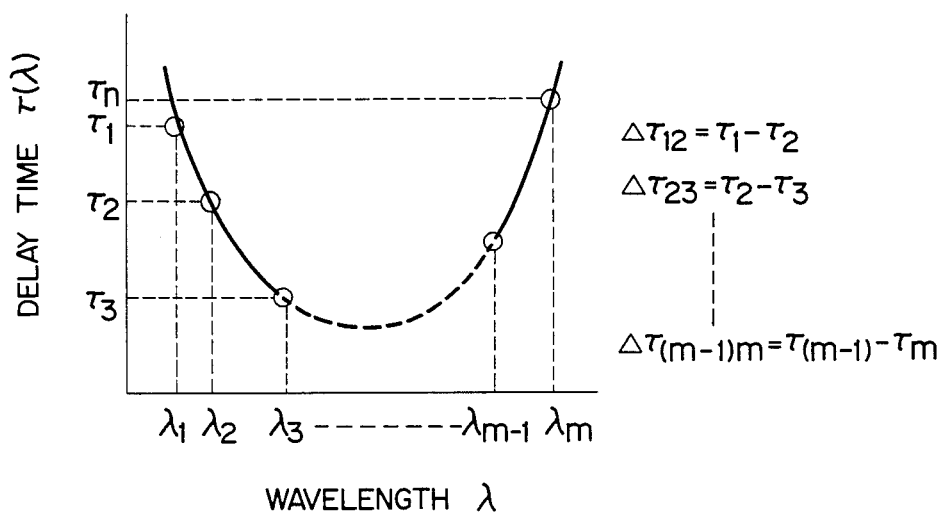
FIG. 2 is a graph showing the relationship between a group delay time difference and wavelengths when chromatic dispersion are measured based on the principle of the present invention.

The baseband phase comparison method of the chromatic dispersion measuring system of the present invention will be described more in detail with reference to the graph shown in FIG. 2. In the system of the present invention, four wavelengths $\lambda_1$ to $\lambda_4$ are used. However, as shown in FIG. 2 a plurality of light sources having m different wavelengths $\lambda_1$ to $\lambda_m$ are assumed. A phase difference between two adjacent wavelengths inside a measuring device (internal phase difference) is given by $\theta'_{(n-1)n}$ (n=2, 3, ..., m), and a phase difference between two adjacent wavelengths in the receiver after transmission through a measurement optical fiber is given by $\theta_{(n-1)n}$ (n=2, 3, ..., m). A modulation frequency is given by f, and a delay time difference is given by $\tau_{(n-)n}$. Therefore, $\theta_{(n-1)n} = \theta'_{(n-1)n} + 2\pi f \tau_{(n-1)n}$ (n=2, 3, ..., m) is established. Assuming that the length of the measurement optical fiber is given by l, and the phase difference between two wavelengths is given by $\phi_{(n-1)n}$, since $\phi_{(n-1)n} = \theta_{(n-1)n} - \theta_{(n-1)n}$, group delay time difference $\Delta\tau_{(n-1)n}$ per unit length can be represented by:

$$\Delta\tau_{(n-1)n} = \frac{\phi_{(n-1)n}}{2\pi f} \frac{1}{l} \quad (n = 2, 3, \ldots, m)$$

The graph in FIG. 2 represents the relationship between group delay time difference $\Delta\tau_{(n-1)n}$ and wavelengths $\lambda_1$ to $\lambda_m$. The curve in FIG. 2 can be represented by some approximating formulas. However, in the chromatic dispersion measuring system of the present invention, since four light sources are used, the following quadratic formula is used:

$$\tau(\lambda) = a\lambda^2 + b + c\lambda^{-2}$$

Phase measurement in the chromatic dispersion characteristic measuring system of the present invention is performed for each combination of four wavelengths $\lambda_1$ to $\lambda_4$ and four modulation frequencies f1 to f4 in association with the above repetitive operation. Of these combinations, data free from phase rotation and having a maximum one of modulation frequencies f1 to f4 is selected, and the group delay time difference between wavelengths is calculated. Based on the measurement result, CPU 53 calculates the quadratic formula $\tau(\lambda) = a\lambda^2 + b + c\lambda^{-2}$ using a least squares method. The resultant quadratic formula is differentiated with wavelength $\lambda$, thus obtaining chromatic dispersion characteristics $D(\lambda) = d(\lambda)/d\lambda$. The measurement result is output to CRT 54 and printer 55 in the form of a graph and numerical values, and can also be output to an external printer/plotter (not shown) via GPIB 56.

As described above, since half mirror 27 is arranged at the output side of laser diode LD4 constituting light source group 25, the optical signal from laser diode LD4 can be branched into two signals so that one signal can be used as the reference optical signal and the other signal can be used as the measurement optical signal. Therefore, a special-purpose light source used only for generating the reference optical signal can be omitted, and the number of light sources can be reduced.

Thus, a low-cost, compact chromatic dispersion measuring system can be provided.

Since programmable optical attenuators 41 and 42 and current monitors 45 and 46 are arranged in optical signal receiver 40, the levels of the optical signals output from reference optical fiber 61 and measurement optical fiber 62 can be automatically adjusted.

Therefore, photoelectric conversion with good linearity can be performed.

One specific embodiment of the present invention has been described. However, various changes and modifications may be made by those who are skilled in the art within the spirit and scope of the invention.

What is claimed is:

1. A light signal transmission apparatus for measuring a chromatic dispersion of an optical fiber based on a baseband phase comparison method, said apparatus comprising:

n light source means for selectively generating optical signals having wavelengths corresponding to n wavelength points to be measured as measurement optical signals, one of said n light source means also serving to generate a reference optical signal;

modulation signal generating means for generating at least one modulation signal having a predetermined frequency;

first control signal generating means for designating said n light source means in a predetermined order in order to generate the measurement optical signals and the reference optical signal;

light source switching means, which is coupled between said first control signal generating means, said modulation signal generating means, and said n light source means, for selectively supplying the modulation signal to a specific one of said n light source means, which is designated by the first control signal to generate the measurement optical signal and to said light source means which also serves to generate the reference optical signal, or only to the light source which serves to generate both the measurement optical signal and the reference optical signal;

second control signal generating means for generating a second control signal having a predetermined synchronous relation with the first control signal; and optical switch means, which has n optical signal inputs arranged in correspondence with said n light source means, a measurement optical signal output, and a reference optical signal output, for, in response to the second control signal from said second control signal generating means, commonly outputting, to the measurement optical signal output, the measurement optical signal which is output from the designated one of said n light source means and is selectively input to the n optical signal inputs, and outputting the reference optical signal generated by one of said n light source means to the reference optical signal output.

2. An apparatus according to claim 1, wherein said n light source means comprise not less than 4 laser diodes.

3. An apparatus according to claim 1, wherein said modulation signal generating means comprises not less than 4 quartz oscillators.

4. An apparatus according to claim 1, wherein said first and second control signal generating means comprise a CPU.

5. An apparatus according to claim 1, wherein said optical switch means comprises a half mirror for branching the reference optical signal generated by one of said n light source means into two signals, outputting one signal of the branched reference optical signals to the measurement optical signal output, and outputting the other signal of the branched reference optical signals to the reference optical signal output.

6. An apparatus according to claim 1, wherein said optical switch means comprises not less than three pairs of parallelogram prisms and triangular prisms for commonly outputting, to the measurement optical signal output, the measurement optical signals incident through the n optical signal inputs of said optical switch means excluding the optical signal input which receives the reference optical signal.

7. An apparatus according to claim 1, wherein said optical switch means comprises: a half mirror for branching the reference optical signal generated by one of said n light source means into two signals, outputting one signal of the branched reference optical signals to the measurement optical signal output, and outputting the other signal of the branched reference optical signals to the reference optical signal output; and not less than three pairs of parallelogram prisms and triangular prisms for commonly outputting, to the measurement optical signal output, the measurement optical signals incident through the n optical signal inputs of said optical switch means excluding the optical signal input which receives the reference optical signal, the pairs of said parallelogram prisms and said triangular prisms being disposed to shield a path of the one signal of the branched reference optical signals to the measurement optical signal output.

8. An apparatus according to claim 1, wherein said light source switching means comprises a 2-branching circuit and a channel switching circuit.

9. A system for measuring a chromatic dispersion of an optical fiber based on a baseband phase comparison method, said system comprising:

a light signal transmitter means comprising n light source means for selectively generating optical signals having wavelengths corresponding to n wavelength points to be measured as measurement optical signals, one of said n light source means also serving to generate a reference optical signal, modulation signal generating means for generating at least one modulation signal having a predetermined frequency, first control signal generating means for designating said n light source means in a predetermined order in order to generate the measurement optical signals and the reference optical signal, light source switching means, which is coupled between said first control signal generating means, said modulation signal generating means, and said n light source means, for selectively supplying the modulation signal to a specific one of said n light source means, which is designated by the first control signal to generate the measurement optical signal and to said light source means which also serves to generate the reference optical signal, or only to the light source which serves to generate both the measurement optical signal and the reference optical signal, second cnotrol signal generating means for generating a second control signal having a predetermined synchronous relation with the first control signal, and optical switch means, which has n optical signal inputs arranged in correspondence with said n light source means, a measurement optical signal output, and a reference optical signal output, for, in response to the second control signal from said second control signal generating means, commonly outputting, to the measurement optical signal output, the measurement optical signal which is output from the designated one of said n light source means and is selectively input to the n optical signal inputs, and outputting the reference optical signal generated by one of said n light source means to the reference optical signal output;

a reference optical fiber having one end and the other end, the one end of said reference optical fiber being coupled to the reference optical signal output of said optical switch means to receive the reference optical signal from the reference optical signal output;

a measurement optical fiber having one end and the other end, the one end of said measurement optical fiber being coupled to the measurement optical signal output so as to receive the measurement optical signal from the measurement optical signal output; and a light signal receiver means, coupled to the other end of said reference optical fiber and the other end of said measurement optical fiber, for receiving the reference optical signal from the other end of said reference optical fiber and the measurement optical signal from the other end of said measurement optical fiber, respectively, and for measuring chromatic dispersion.

10. A system according to claim 9, wherein said n light source means comprise not less than 4 laser diodes.

11. A system according to claim 9, wherein said modulation signal generating means comprises not less than 4 quartz oscillators.

12. A system according to claim 9, wherein said first and second control signal generating means comprise a CPU.

13. A system according to claim 9, wherein said optical switch means comprises a half mirror for branching the reference optical signal generated by one of said n light source means into two signals, outputting one signal of the branched reference optical signals to the measurement optical signal output, and outputting the other signal of the branched reference optical signals to the reference optical signal output.

14. A system according to claim 9, wherein said optical switch means comprises not less than three pairs of parallelogram prisms and triangular prisms for commonly outputting, to the measurement optical signal output, the measurement optical signals incident through the n optical signal inputs of said optical switch means excluding the optical signal input which receives the reference optical signal.

15. A system according to claim 9, wherein said optical switch means comprises: a half mirror for branching the reference optical signal generated by one of said n light source means into two signals, outputting one signal of the branched reference optical signals to the measurement optical signal output, and outputting the other signal of the branched reference optical signals to the reference optical signal output; and not less than three pairs of parallelogram prisms and triangular prisms for commonly outputting, to the measurement optical signal output, the measurement optical signals incident through the n optical signal inputs of said optical switch means excluding the optical signal input which receives the reference optical signal, the pairs of said parallelogram prisms and said triangular prisms being disposed to shield a path of the one signal of the branched reference optical signals to the measurement optical signal output.

16. A system according to claim 9, wherein said light source switching means comprises a 2-branching circuit and a channel switching circuit.

17. A system for measuring a chromatic dispersion of an optical fiber based on a baseband phase comparison method, said system comprising:

a light signal transmitter means comprising n light source means for selectively generating optical signals having wavelengths corresponding to n wavelength points to be measured as measurement optical signals, one of said n light source means also serving to generate a reference optical signal, modulation signal generating means for generating at least one modulation signal having a predetermined frequency, first control signal generating means for designating said n light source means in a predetermined order in order to generate the measurement optical signals and the reference optical signal, light source switching means, which is coupled between said first control signal generating means, said modulation signal generating means, and said n light source means, for selectively supplying the modulation signal to a specific one of said n light source means, which is designated by the first control signal to generate the measurement optical signal and to said light source means which also serves to generate the reference optical signal, or only to the light source which serves to generate both the measurement optical signal and the reference optical signal, second control signal generating means for generating a second control signal having a predetermined synchronous relation with the first control signal, and optical switch means, which has n optical signal inputs arranged in correspondence with said n light source means, a measurement optical signal output, and a reference signal optical output, for, in response to the second control signal from said second control signal generating means, commonly outputting, to the measurement optical signal output, the measurement optical signal which is output from the designated one of said n light source means and is selectively input to the n optical signal inputs, and outputting the reference optical signal generated by one of said n light source means to the reference optical signal output;

a reference optical fiber having one end and the other end, the one end of said reference optical fiber being coupled to the reference optical signal output of said optical switch means to receive the reference optical signal from the reference optical signal output;

a measurement optical fiber having one end and the other end, the one end of said measurement optical fiber being coupled to the measurement optical signal output so as to receive the measurement optical signal from the measurement optical signal output; and a light signal receiver means, coupled to the other end of said reference optical fiber and the other end of said measurement optical fiber, for receiving the reference optical signal from the other end of said reference optical fiber and the measurement optical signal from the other end of said measurement optical fiber and for measuring chromatic dispersion, said receiver means including a plurality of programmable optical attenuator means for automatically adjusting the levels of the reference optical signal and the measurement optical signal.

18. A system according to claim 17, wherein said n light source means comprise not less than 4 laser diodes.

19. A system according to claim 17, wherein said modulation signal generating means comprises not less than 4 quartz oscillators.

20. A system according to claim 17, wherein said first and second control signal generating means comprise a CPU.

21. A system according to claim 17, wherein said optical switch means comprises a half mirror for branching the reference optical signal generated by one of said n light source means into two signals, outputting one signal of the branched reference optical signals to the measurement optical signal output, and outputting the other signal of the branched reference optical signals to the reference optical signal output.

22. A system according to claim 17, wherein said optical switch means comprises not less than three pairs of parallelogram prisms and triangular prisms for commonly outputting, to the measurement optical signal output, the measurement optical signals incident through the n optical signal inputs of said optical switch means excluding the optical signal input which receives the reference optical signal.

23. A system according to claim 17, wherein said optical switch means comprises: a half mirror for branching the reference optical signal generated by one of said n light source means into two signals, outputting one signal of the branched reference optical signals to the measurement optical signal output, and outputting the other signal of the branched reference optical signals to the reference optical signal output; and not less than three pairs of parallelogram prisms and triangular prisms for commonly outputting, to the measurement optical signal output, the measurement optical signals incident through the n optical signal inputs of said optical switch means excluding the optical signal input which receives the reference optical signal, the pairs of said parallelogram prisms and said triangular prisms being disposed to shield a path of the one signal of the branched reference optical signals to the measurement optical signal output.

24. A system according to claim 17, wherein said light source switching means comprises a 2-branching circuit and a channel switching circuit.

25. A system according to claim 17, wherein said plurality of programmable optical attenuator means comprise photoelectric converters for converting the reference optical signal and the measurement optical signal into electrical signals, respectively, current monitors coupled with said photoelectric converters for detecting levels of the electrical signals from said photoelectric converters and for generating control signals corresponding to the detected levels of the electrical signals from said photoelectric converters, and programmable optical attenuators coupled with said photoelectric converters for automatically adjusting the levels of the reference optical signal and the mesurement optical signal.

* * * * *